United States Patent
Zeng et al.

(10) Patent No.: US 9,782,256 B2
(45) Date of Patent: Oct. 10, 2017

(54) HEART VALVE ASSEMBLY

(71) Applicant: Horizon Scientific Corp., Irvine, CA (US)

(72) Inventors: Min Frank Zeng, Irvine, CA (US); Pham Lo, Irvine, CA (US)

(73) Assignee: Venus Medtech (Hangzhou) Inc (CN)

( * ) Notice: Subject to any disclaimer, the term of this patent is extended or adjusted under 35 U.S.C. 154(b) by 60 days.

(21) Appl. No.: 14/696,645

(22) Filed: Apr. 27, 2015

(65) Prior Publication Data

US 2016/0310267 A1    Oct. 27, 2016

(51) Int. Cl.
*A61F 2/24* (2006.01)

(52) U.S. Cl.
CPC .............. *A61F 2/2418* (2013.01); *A61F 2/24* (2013.01); *A61F 2/2409* (2013.01); *A61F 2/2436* (2013.01); *A61F 2220/0008* (2013.01); *A61F 2220/0075* (2013.01); *A61F 2230/0052* (2013.01); *A61F 2230/0065* (2013.01); *A61F 2250/0039* (2013.01); *A61F 2250/0069* (2013.01)

(58) Field of Classification Search
CPC ........ A61F 2/24; A61F 2/2418; A61F 2/2409; A61F 2/2412
See application file for complete search history.

(56) References Cited

U.S. PATENT DOCUMENTS

| | | |
|---|---|---|
| 2004/0092858 A1 | 5/2004 | Wilson et al. |
| 2005/0043790 A1 | 2/2005 | Seguin |
| 2013/0310928 A1 | 11/2013 | Morriss et al. |
| 2014/0330371 A1* | 11/2014 | Gloss .................... A61F 2/2418 623/2.17 |

OTHER PUBLICATIONS

International Search Report and Written Opinion dated Oct. 17, 2016 for PCT/US16/29196.

* cited by examiner

*Primary Examiner* — David Isabella
*Assistant Examiner* — Dinah Baria
(74) *Attorney, Agent, or Firm* — Raymond Sun

(57) ABSTRACT

A heart valve assembly has a heart valve assembly that has an anchor section, a generally cylindrical valve support section, and a neck section that transitions between the anchor section and the valve support section. A plurality of supports extend radially outwardly in an annular manner about an upper end of the valve support section, and the anchor section has an annular flange that extends radially therefrom, so that an annular space is defined between the annular flange and the annular supports for receiving or capturing the native annulus when the heart valve is deployed. The heart valve assembly also includes a leaflet assembly having a plurality of leaflets that are stitched to the valve support section and which are positioned on an inflow side of the neck section.

13 Claims, 14 Drawing Sheets

FIG 8C.
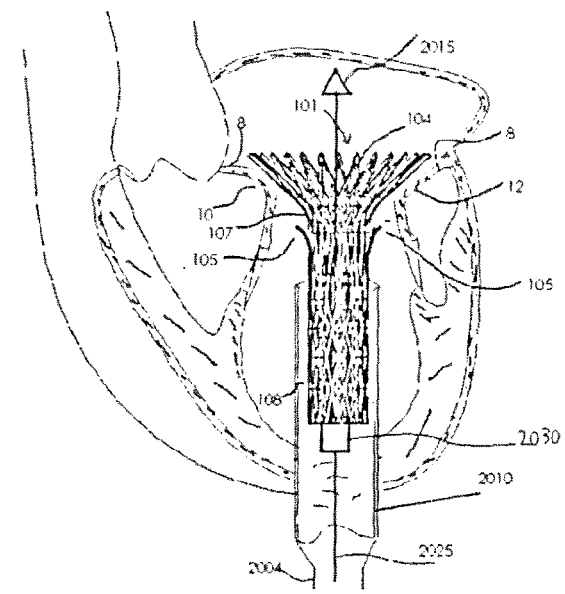
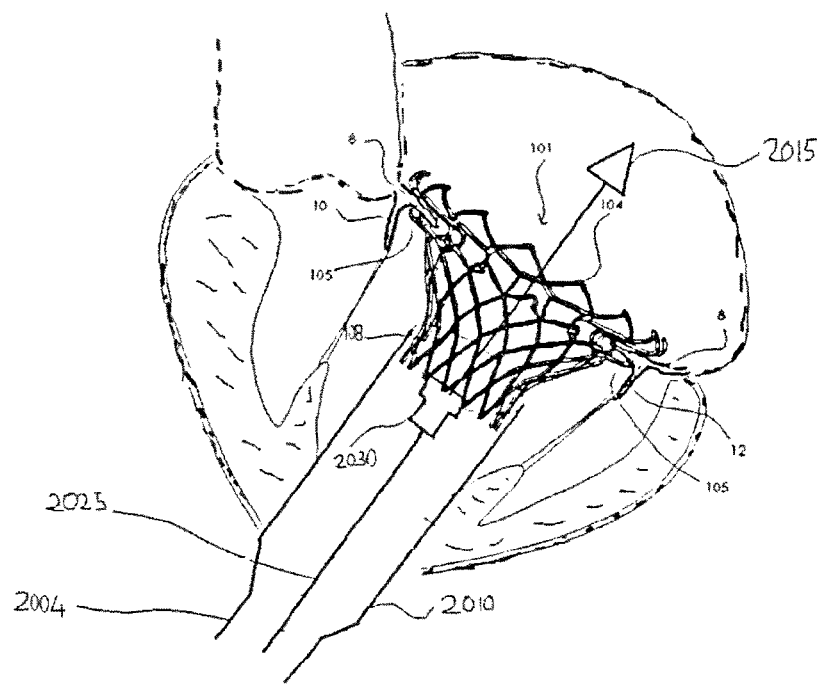
FIG 8D.

HEART VALVE ASSEMBLY

BACKGROUND OF THE INVENTION

1. Field of the Invention

The present invention is directed to methods, systems, and apparatus for safely replacing or repairing native heart valves with prosthetic heart valves.

2. Description of the Prior Art

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Unlike the aortic valve, however, the mitral valve annulus does not provide a good landmark for positioning a replacement mitral valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement mitral valve in the native mitral valve annulus. The general anatomy of the mitral valve annulus also makes it more difficult to properly anchor a replacement mitral valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

Thus, the larger mitral valve annulus makes it difficult to securely implant current percutaneously delivered valves in the native mitral position. Some attempts have been made to deliver and implant a one-piece replacement mitral valve, but it is difficult to provide a device that can be collapsed down to have a sufficiently small delivery profile and still be able to be expanded and secured in place within the mitral valve via a vascular access site.

As a result, there remains a need for a replacement mitral valve that has a valve support structure or anchoring device that can be positioned near or within the native mitral valve.

SUMMARY OF THE DISCLOSURE

To accomplish the objectives set forth above, the present invention provides a heart valve assembly that has a wire frame comprising an anchor section, a generally cylindrical valve support section, and a neck section that transitions between the anchor section and the valve support section. The wire frame includes a plurality of supports extending radially outwardly in an annular manner about an upper end of the valve support section, and the anchor section has an annular flange that extends radially therefrom, so that an annular space is defined between the annular flange and the annular supports for receiving or capturing the native annulus when the heart valve is deployed. The heart valve assembly also includes a leaflet assembly having a plurality of leaflets that are stitched to the valve support section and which are positioned on an inflow side of the neck section. The heart valve assembly can be secured at the location of the native annulus of a human heart by delivering the heart valve assembly to the location of a native annulus, and deploying the heart valve assembly at the location of the native annulus with the native annulus retained inside the annular space.

BRIEF DESCRIPTION OF THE DRAWINGS

FIGS. 8A-8E illustrate how the device of FIG. 1 can be deployed at the mitral annulus of a patient's heart using a transapical delivery system.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
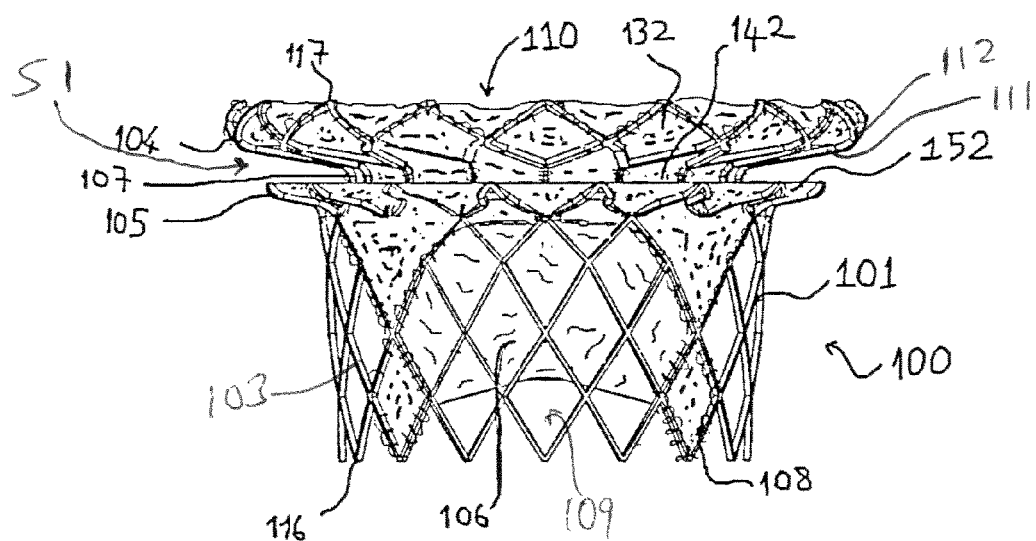
FIG. 1 is a side view of a valve device according to one embodiment of the present invention shown in an expanded configuration.
Figure 2:
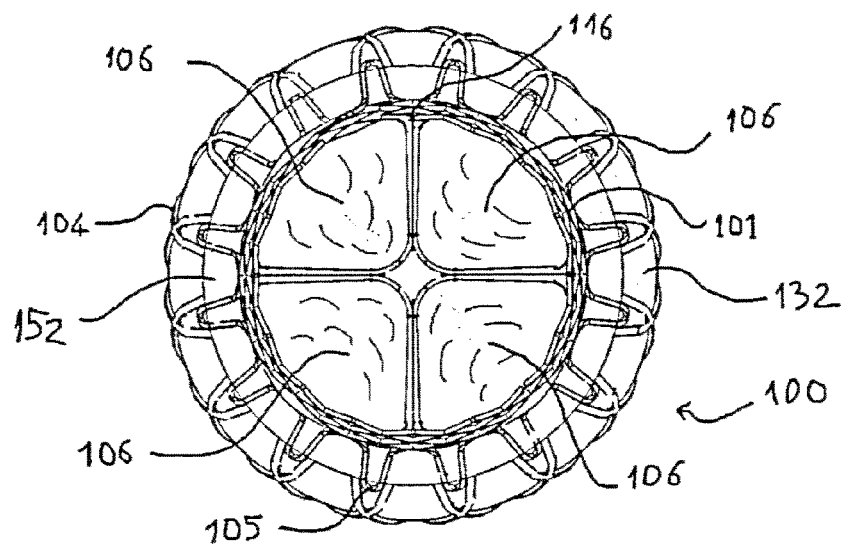
FIG. 2 is a bottom view of the device of FIG. 1, shown with the valve in a fully closed position with pressure on the leaflets.
Figure 3:
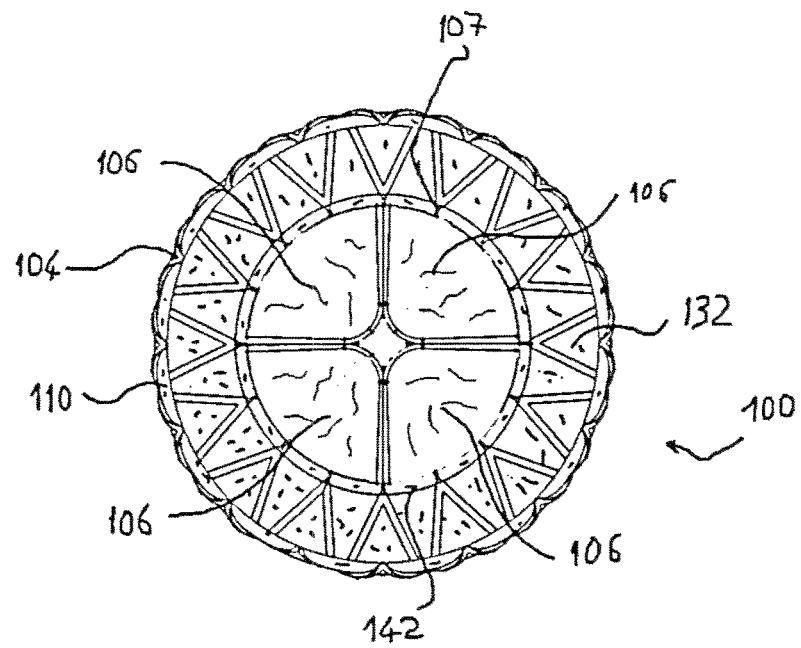
FIG. 3 is a top view of the device of FIG. 1, shown with the valve in a fully closed position with pressure on the leaflets.

The present invention provides a mitral valve device 100 that is shown in fully assembled form in FIGS. 1-3. The device 100 has a wire frame 101 (see FIGS. 4-6) that is adapted to carry an integrated leaflet assembly that comprises a plurality of leaflets 106. The wire frame 101 provides a simple leaflet valve support structure that can be effectively secured at the native mitral valve annulus. The overall construction of the device 100 is simple, and effective in promoting proper mitral valve function.

Figure 4:
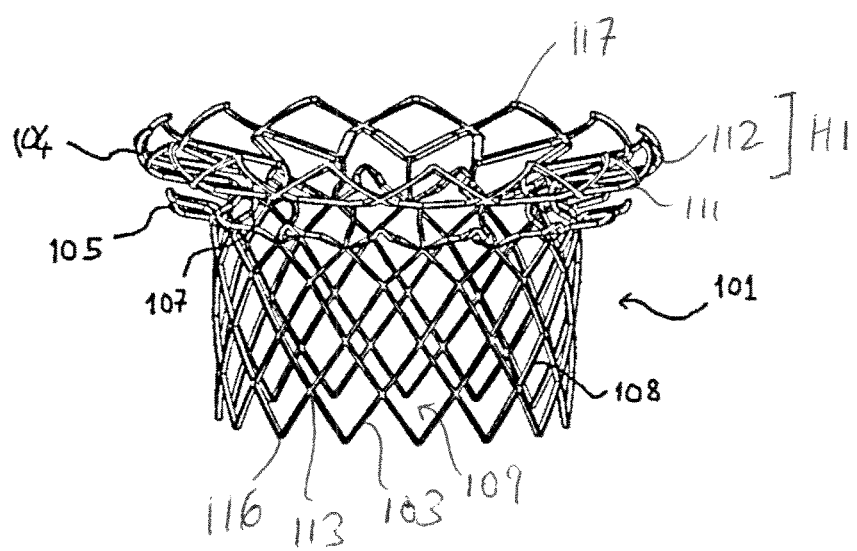
FIG. 4 is a side view of the wire frame of the device of FIG. 1.
Figure 5:
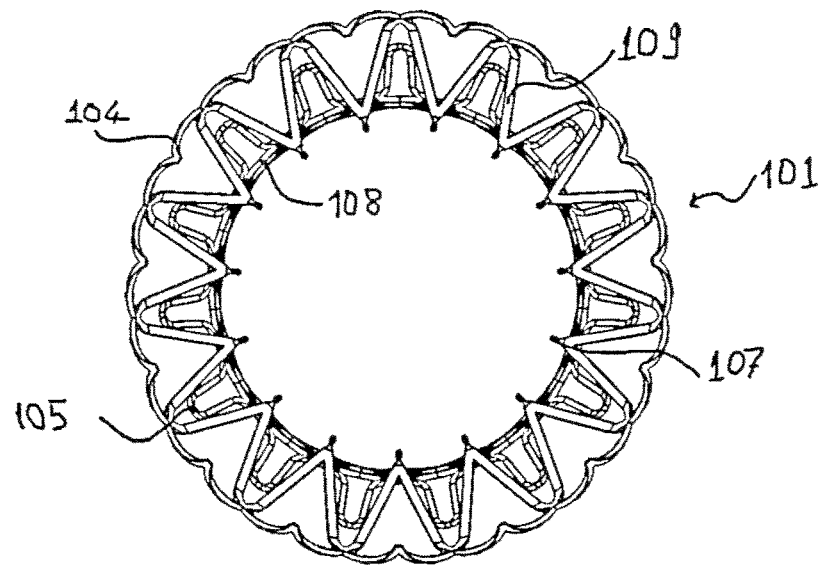
FIG. 5 is a top view of the wire frame of FIG. 4.
Figure 6:
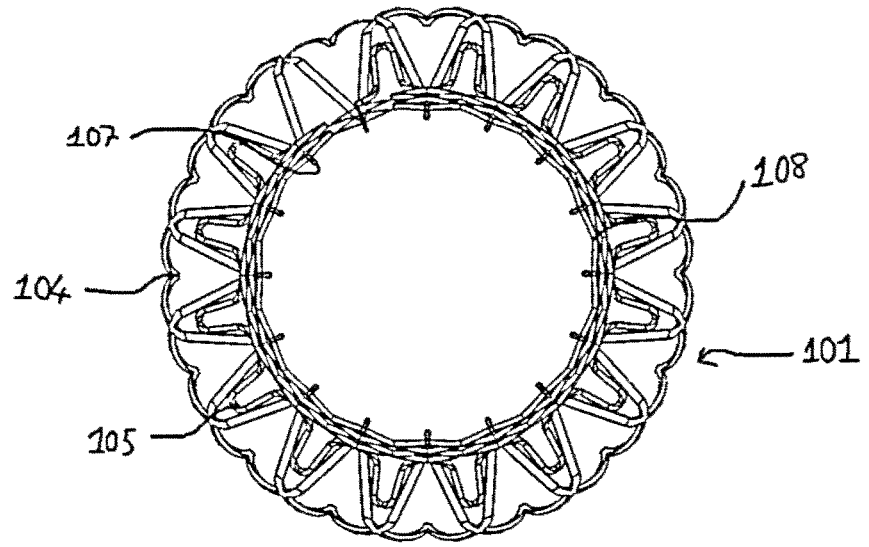
FIG. 6 is a bottom view of the wire frame of FIG. 4.

As shown in FIGS. 4-6, the wire frame 101 comprises an (outflow) anchor section 104 that transitions to a generally cylindrical valve support section 108 via a neck section 107. The different sections 104, 107 and 108 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.2" to 0.4". These sections 104, 107 and 108 define open cells 109 within the wire frame 101. Each cell 109 can be defined by a plurality of struts 103 that encircle the cell. In addition, the shapes and sizes of the cells 109 can vary between the different sections 104, 107 and 108.

The valve support section 108 functions to hold and support the leaflets 106, and has an inflow end that is configured with an annular zig-zag arrangement of inflow tips 116. The zig-zag arrangement defines peaks (i.e., the tips 116) and valleys (inflection points 113). As shown in FIG. 1, the leaflets 106 can be sewn directly to the struts 103 of the cells 109 in the valve support section 108.

A plurality of V-shaped annular supports 105 extend radially outwardly in an annular manner about the upper end of the valve support section 108. These supports 105 extend radially outwardly and upwardly at a slight angle. The upper end of the valve support 108 also transitions into the neck section 107 which first extends radially inwardly, and then continues to curve back radially outwardly as it transitions into the anchor section 104. In other words, the neck section 107 is configured as an annular U-shaped section.

The anchor section 104 functions to secure or anchor the valve device 100, and specifically the wire frame 101, to the native valve annulus of the human heart. The anchor 104 has a flared and bowl-shaped configuration where it defines an annular flange 111 that extends radially outwardly from the neck section 107 to an outer-most annular line 112 where its diameter is greatest, and then curves radially inwardly to an annular zig-zag arrangement of outflow tips 117 at its uppermost periphery. The zig-zag arrangement defines peaks (i.e., the tips 117) and valleys. All portions of the anchor section 104 have a wider diameter than the neck section 107 and valve support section 108. The outer diameter of the V-shaped supports 105 is also less than the outer-most diameter of the anchor section 104 at the annular line 112. An annular space S1 is defined between the flange 111 and the V-shaped supports 105.

The following are some exemplary and non-limiting dimensions for the device 100. For example, the outer diameter for the annular line 112 can be 50 mm; the outer diameter of the V-shaped supports 105 can be 40 mm; the inner diameter of the neck section 107 can be 30 mm; and the outer diameter of the valve support section 108 can be 30 mm. In addition, the length of the valve support section 108 can vary depending on the number of leaflets 106 are supported therein. For example, in the embodiment illustrated in FIGS. 1-3 where four leaflets 106 are provided, the length of the valve support section 108 can be about 12-14 mm. If three leaflets 106 are provided, the length of the valve support section 108 would need to be longer, such as 15-18 mm. The height of the space S1 can be 5 mm, and the height H1 of the anchor section 104 can be 5 mm. These exemplary dimensions can be used for a device 100 that is adapted for use at the native mitral valve location for a generic adult and these dimensions will vary for devices 100 that are used for other applications, such as for an aortic or tricuspid valve. These exemplary dimensions illustrate the proportions of the various elements to each other.

Referring to FIGS. 1-3, the leaflet assembly includes the actual leaflets 106 as well as a number of skirts. For example, an upper skirt 132 can be sewn to the struts 103 in the anchor section 104 to cover the flange 111 and the rest of the anchor section 104; an intermediate neck skirt 142 can be sewn to the struts 103 in the neck section 107 to cover the neck section 107, and a lower annulus skirt 152 can be sewn to the V-shaped supports 105 to cover the cells in the V-shaped supports 105. The leaflets 106 can be sewn directly to the struts 103 of the cells 109 in the valve support section 108. The leaflets 106 and the skirts 132, 142 and 152 can be made of the same material. For example, the material can be a treated animal tissue such as pericardium, or from biocompatible polymer material (such as PTFE, Dacron, bovine, porcine, etc.). The leaflets 106 and the skirts 132, 142 and 152 can also be provided with a drug or bioagent coating to improve performance, prevent thrombus formation, and promote endothelialization, and can also be treated (or be provided) with a surface layer/coating to prevent calcification.

The device 100 of the present invention can be compacted into a low profile and loaded onto a delivery system, and then delivered to the target location by a non-invasive medical procedure, such as through the use of a delivery catheter through transapical, or transfemoral, or transseptal procedures. The device 100 can be released from the delivery system once it reaches the target implant site, and can expand to its normal (expanded) profile either by inflation of a balloon (for a balloon expandable wire frame 101) or by elastic energy stored in the wire frame 101 (for a device where the wire frame 101 is made of a self-expandable material).

Figure 7:
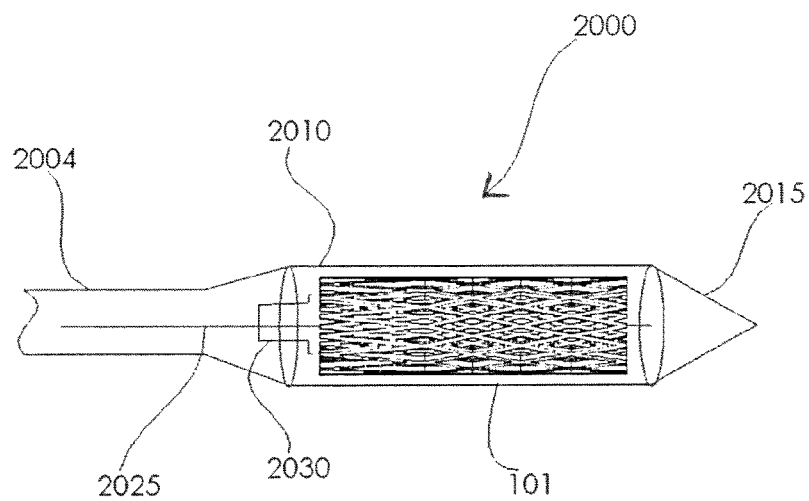
FIG. 7 illustrates a delivery system that can be used to deploy the device of FIG. 1.

FIGS. 8A-8E illustrate how the device 100 can be deployed at the mitral annulus of a patient's heart using a transapical delivery. Referring first to FIG. 7, the delivery system includes a delivery catheter 2000 that has a distal tip 2015 which is connected to the ear hub 2030 of the inner core 2025. The catheter 2000 has an outer shaft 2004 that is connected to a handle (not shown), and the outer shaft 2004 includes a capsule 2010. The device 100 is crimped and loaded on the inner core 2025 below the tip 2015, and then covered by the capsule 2010.

Figure 8A:
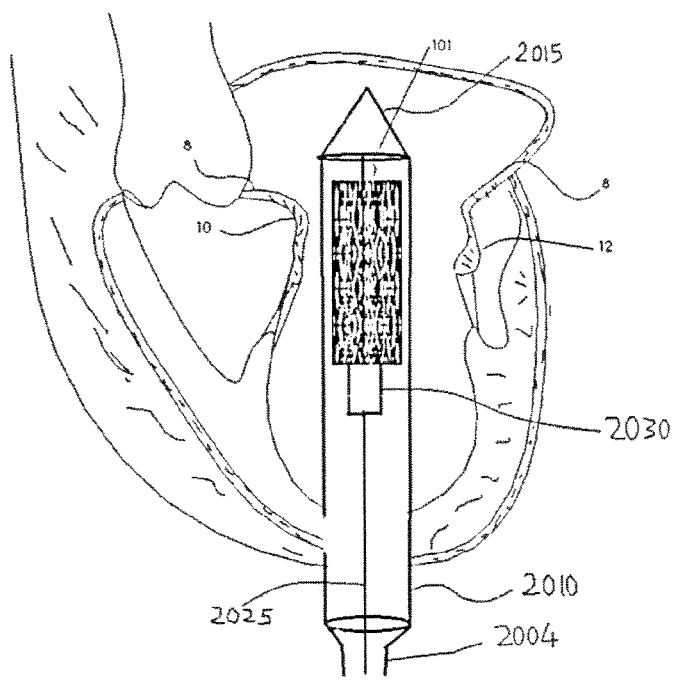
Figure 8B:
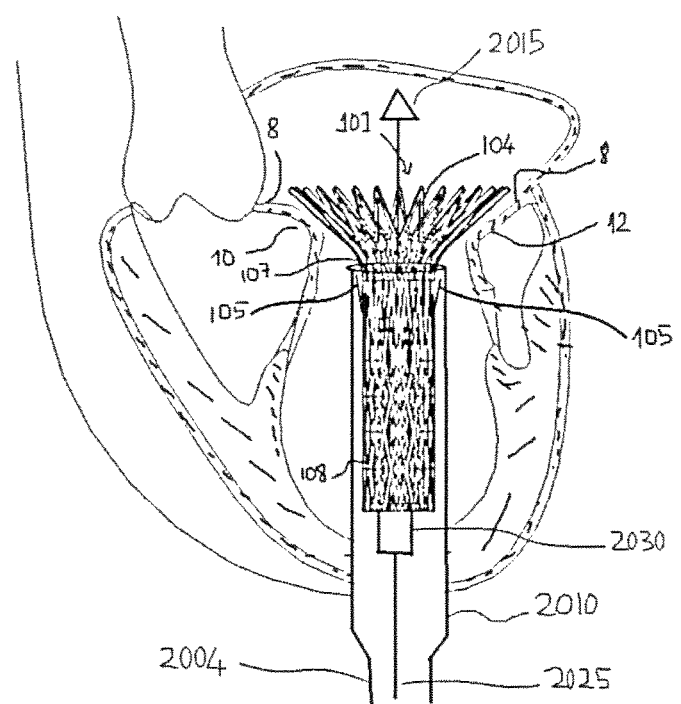
Figure 8E:
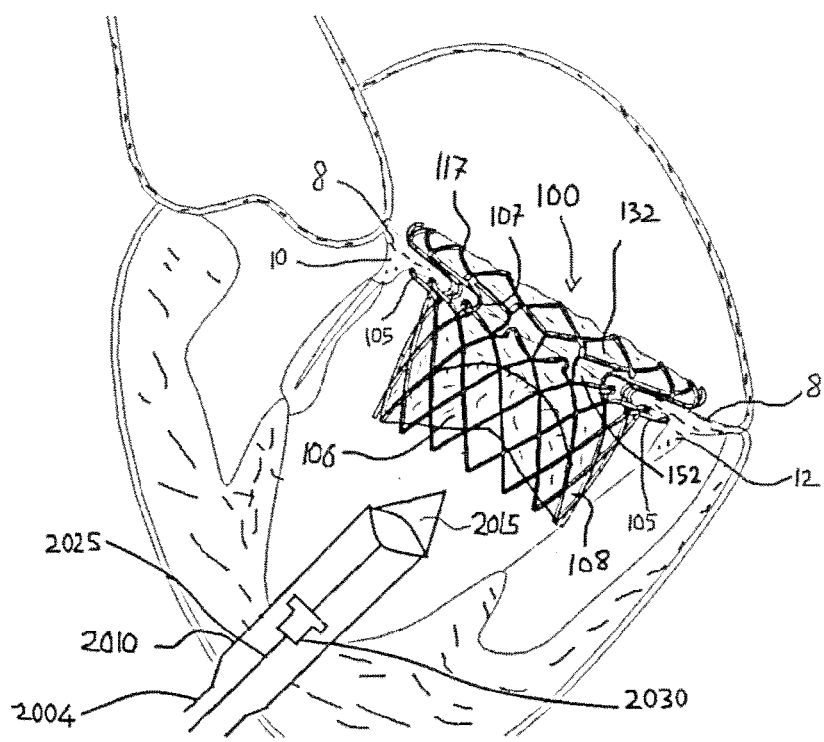
Figure 9:
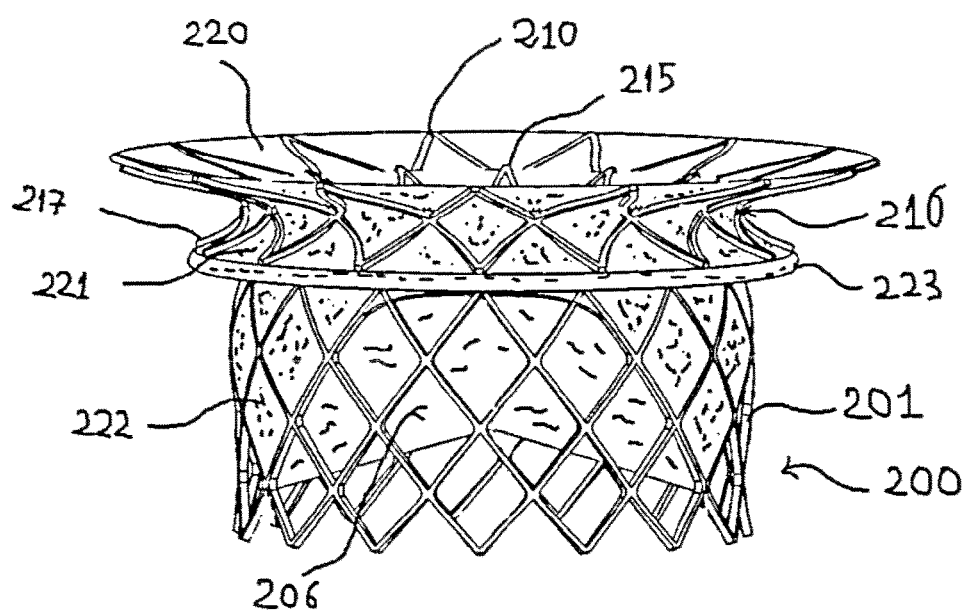
FIG. 9 is a side view of a valve device according to another embodiment of the present invention shown in an expanded configuration.
Figure 10:
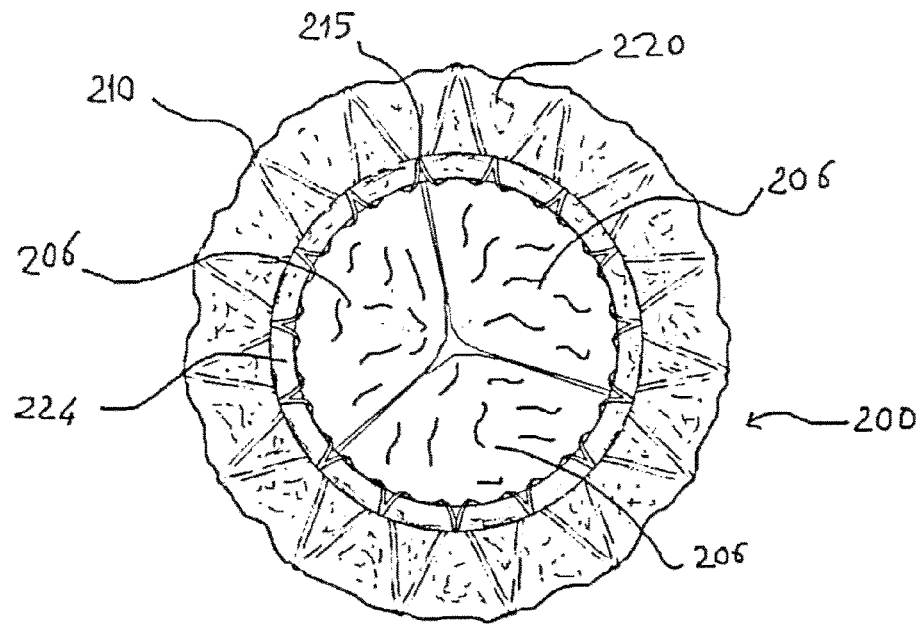
FIG. 10 is a top view of the device of FIG. 9, shown with the valve in a fully closed position with pressure on the leaflets.

Referring now to FIG. 8A, the device 100 is shown in a collapsed configuration being delivered to the mitral annulus inside the capsule 2010. In FIG. 8B, the capsule 2010 is withdrawn (i.e., moved downwardly) with respect to the inner core 2025 (and the device 100 that is carried on the inner core 2025) to partially expose the device 100 so that the self-expanding wire frame 101 will deploy the anchor section 104 in the atrium, and at a location above the native annulus 8. In FIG. 8C, the capsule 2010 is shown as being further withdrawn to release the V-shaped supports 105 at a location below the native annulus 8. This will allow the native annulus 8 to be captured or received in the space S1 between the flange 111 and the V-shaped supports 105. In FIG. 8D, the capsule 2010 is shown as being further withdrawn to release the valve support section 108. FIG. 8E shows the device 100 being fully deployed at the native annulus 8, and with the distal tip 2015 and capsule 2010 being withdrawn with the rest of the delivery system.

Thus, when the device 100 is deployed, the native annulus 8 is captured or received in the space S1 to create a "seal" to prevent leakage (blood flow back from the left ventricle to the left atrium) from the area surrounding the device 100. In addition, the V-shaped supports 105 push aside the native anterior leaflet 10 and the native posterior leaflet 12 against the wall of the ventricle.

FIGS. 9-14 illustrate a second embodiment of a mitral valve device 200 that is shown in fully assembled form in FIGS. 9, 10, 11A and 11B. The device 200 is similar to the device 100 above, except that the one-piece wire frame 101 is now replaced by a wire frame that is made up of two separate pieces: an anchor piece 204 (see FIG. 13) and a valve support piece 208 (see FIG. 14) that can be fitted together. The combined anchor piece 204 and valve support piece 208 is also adapted to carry an integrated leaflet assembly that comprises a plurality of leaflets 206.

Figure 12:
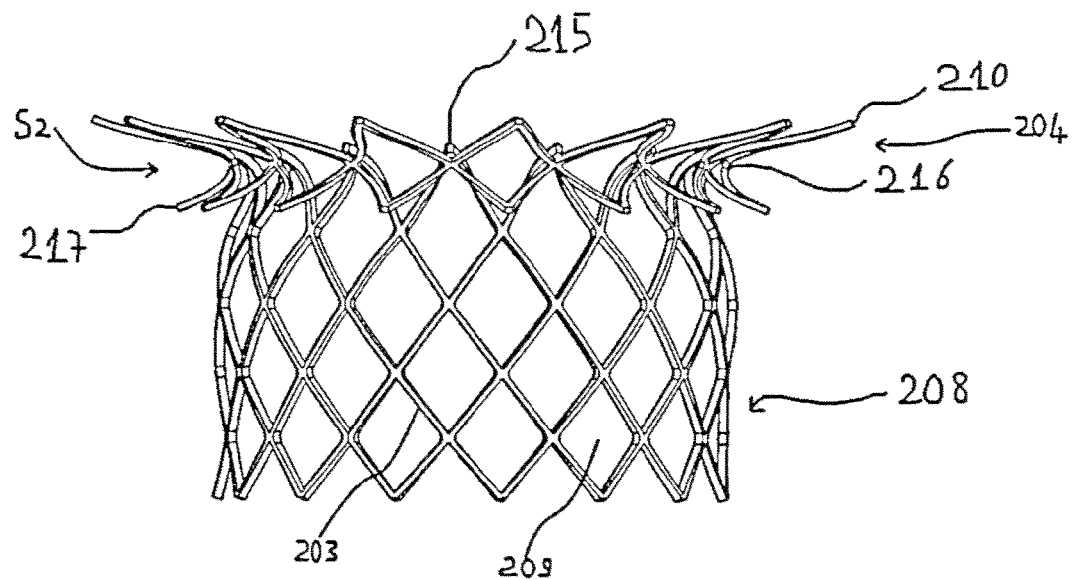
FIG. 12 is a side view of the wire frame of the device of FIG. 9.
Figure 13:
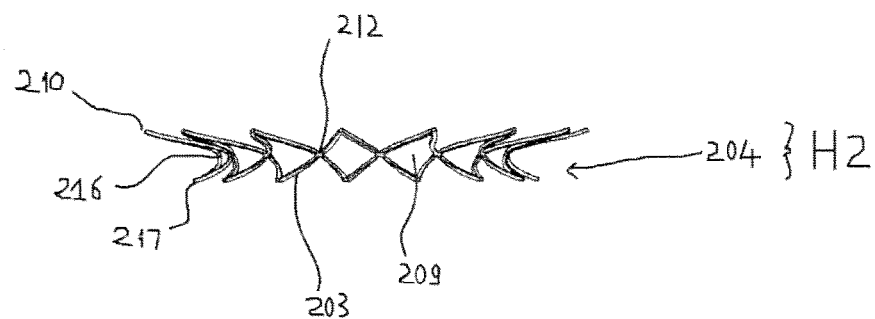
FIG. 13 is a side view of the anchor piece of the wire frame of FIG. 12.
Figure 14:
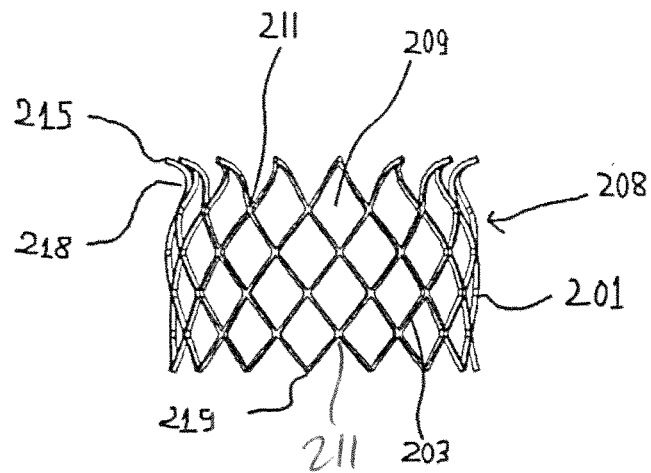
FIG. 14 is a side view of the valve support piece of the wire frame of FIG. 12.

As shown in FIGS. 12-14, the wire frame comprises an anchor piece 204 and a valve support piece 208. Each piece 204 and 208 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.2" to 0.4". These pieces 204 and 208 also define open cells 209 within the wire frame. Each cell 209 can be defined by a plurality of struts 203 that encircle the cell. In addition, the shapes and sizes of the cells 209 can vary between the different pieces 204 and 208.

Referring to FIG. 14, the valve support piece 208 functions in the same way as the valve support section 108, which is to hold and support the leaflets 206. The valve support piece 208 is defined by a cylindrical body 201, and has an inflow end that is configured with an annular zig-zag arrangement of inflow tips 219. At its opposite end, a neck area 218 is defined by an annular concave (U-shaped) section of the cylindrical body 201, and terminates at an outflow end that is configured with an annular zig-zag arrangement of outflow tips 215. The zig-zag arrangement defines peaks (i.e., the tips 215 and 219) and valleys (inflection points 211).

Referring to FIG. 13, the anchor piece 204 also functions to secure or anchor the valve device 200, and specifically the wire frame, to the native valve annulus 8 of the human heart. The anchor piece 204 comprises an annular ring of cells 209 that are configured to define an annular concave (U-shape) belt having an annular zig-zag arrangement of inflow tips 217, and an annular zig-zag arrangement of outflow tips 210, with a neck region 216 defined therebetween. The zig-zag arrangement defines peaks (i.e., the tips 210 and 217) and valleys (inflection points 212).

As best shown in FIG. 12, the anchor piece 204 is coupled to the valve support piece 208 by inserting the outflow end of the valve support piece 208 through the anchor piece 204, with the tips 215 engaging the inflection points 212 between adjacent tips 210 on the anchor piece 204. When the pieces 204 and 208 so are coupled in the manner shown in FIG. 12, the neck region 216 functions in the same way as the neck section 107, and the tips 217 function in the same manner as the V-shaped supports 105. The outer diameters defined by the tips 210 and 217 of the anchor piece 204 are wider than the largest diameter of any part of the body 201 of the valve support piece 208. The outer diameter defined by the tips 217 is also less than the outer diameter defined by the tips 210. An annular space S2 is defined between the tips 210 and 217.

The following are some exemplary and non-limiting dimensions for the device 200. For example, the outer diameter defined by the tips 210 can be 50 mm; the outer diameter defined by the tips 217 can be 40 mm; the inner diameter of the neck region 216 can be 30 mm; and the outer diameter of the cylindrical body 210 of the valve support piece 208 can be 30 mm. In addition, the length of the valve support piece 208 can vary depending on the number of leaflets 206 are supported therein. For example, in the embodiment illustrated in FIGS. 9-11C where three leaflets 206 are provided, the length of the cylindrical body 201 can be about 15-20 mm. If four leaflets 206 are provided, the length of the valve support piece 208 could be shorter, such as less then 14 mm. The height of the space 32 can be 5 mm and the height H2 of the anchor piece 204 can be 10 mm. These exemplary dimensions can be used for a device 200 that is adapted for use at the native mitral valve location for a generic adult and these dimensions will vary for devices 200 that are used for other applications, such as for an aortic or tricuspid valve. These exemplary dimensions illustrate the proportions of the various elements to each other.

Figure 11A:
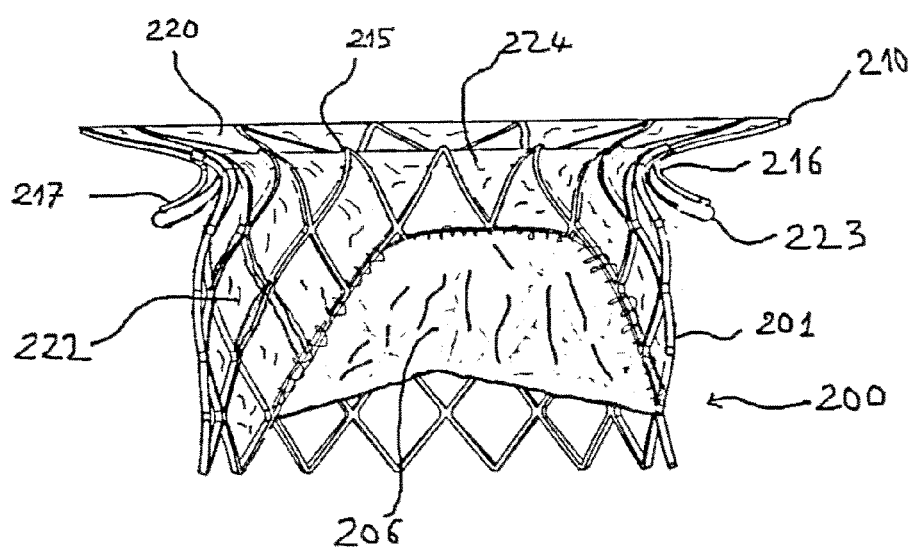
FIG. 11A is a cut-away side view of the device of FIG. 9 after it has implanted in a native valve annulus.
Figure 11B:
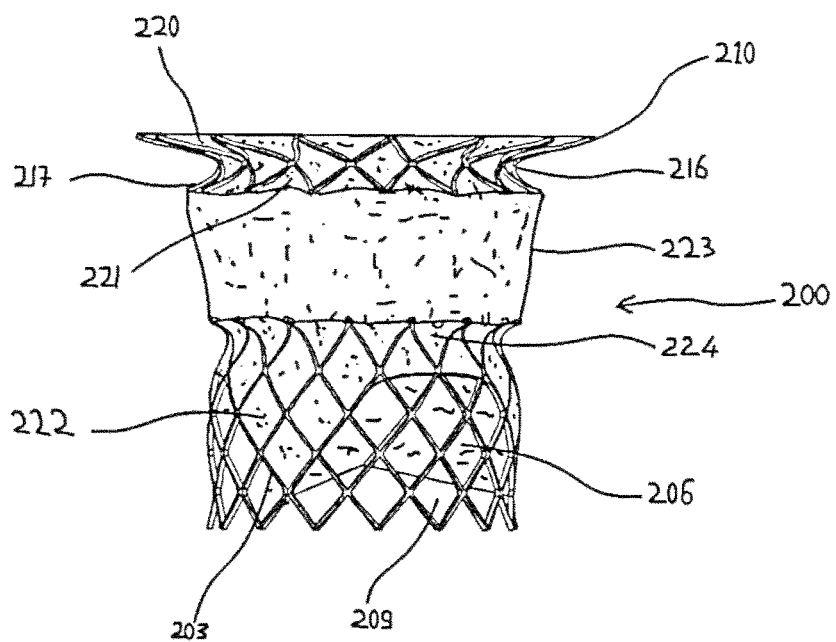
FIG. 11B is a side view of the device of FIG. 9 before it has implanted in a native valve annulus.
Figure 11C:
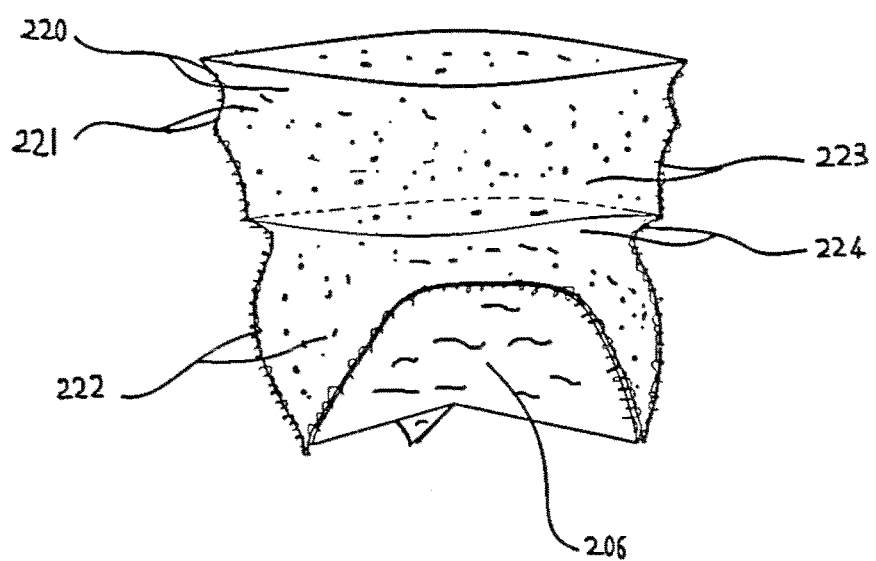
FIG. 11C is a side view of the valve assembly for the device of FIG. 9.

Referring to FIGS. 9, 10, 11A, 11B and 15, the leaflet assembly includes the actual leaflets 206 as well as a number of skirts. For example, an upper annulus skirt 220 can be sewn to the struts 203 in the anchor piece 204 to cover the cells 209 and spaces between the tips 210; a lower annulus skirt 221 can be sewn to the struts 203 in the anchor piece 204 to cover the spaces between the tips 217; a valve support skirt 222 can be sewn to the struts 203 to cover the cells 209 in the cylindrical body 201; a connection skirt 223 can be sewn to the anchor piece 204 and the valve support piece 208 to connect these two pieces 204 and 208; and a valve seal skirt 224 can be sewn to the cells 209 in the neck area 218 extending from the inflection points 211 to the tips 215. As best shown in FIGS. 11A-11C, the connection skirt 223 can be sewn inside the anchor piece 204 and continue down the inner surface of the valve support piece 208. The valve support piece 208 can be inserted inside the anchor piece 204, and the connection skirt 223 can be folded outside the valve support piece 208 at the location of the tips 215 at the neck area 218 to create two layers of the connection skirt 223 at the location of the neck area 218. In fact, the neck region 216 of the anchor piece 204 actually has three layers of skirt material (i.e., tissue): the lower annulus skirt 221 and the overlapping layers of the connection skirt 223. These three layers provide a better seal. The leaflets 206 can be sewn directly to the struts 203 of the cells 209 in the cylindrical body 201. The leaflets 206 and the skirts 220, 221, 222, 223 and 224 can be made of the same material(s) as those described connection with the leaflets 106 above.

As with the device 100, the device 200 can be compacted into a low profile and loaded onto a delivery system, and then delivered to the target location by a non-invasive medical procedure, such as through the use of a delivery catheter through transapical, or transfemoral, or transseptal procedures. The device 200 can be released from the delivery system once it reaches the target implant site, and can expand to its normal (expanded) profile either by inflation of a balloon, or by elastic energy stored in the wire frame 101.

Figure 15:
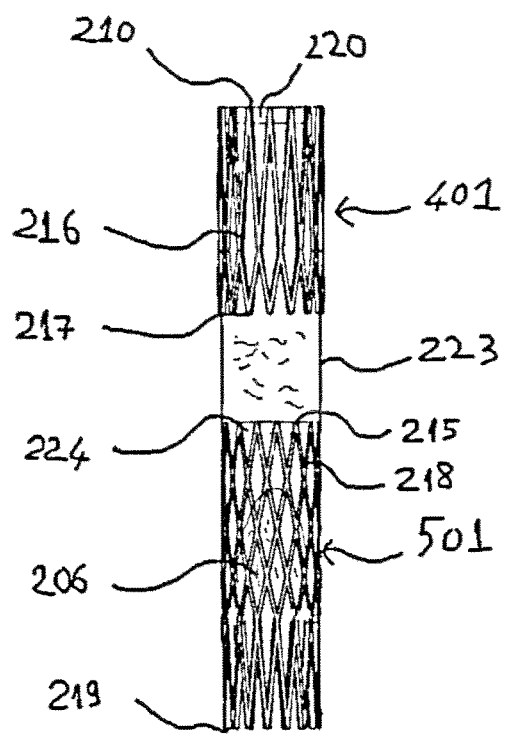
FIG. 15 illustrates the device of FIG. 9 in a compressed configuration.

FIGS. 16A-16D illustrate how the device 200 can be deployed at the mitral annulus of a patient's heart using a transapical delivery, and the delivery catheter 2000 of FIG. 7. Referring first to FIG. 15, the device 200 is shown in its compressed configuration. The device 200 as collapsed can be loaded inside the same delivery catheter 2000 that is shown and described in FIG. 7. The device 200 can be crimped and loaded on the inner core 2025 below the tip 2015, and then covered by the capsule 2010.

Figure 16A:
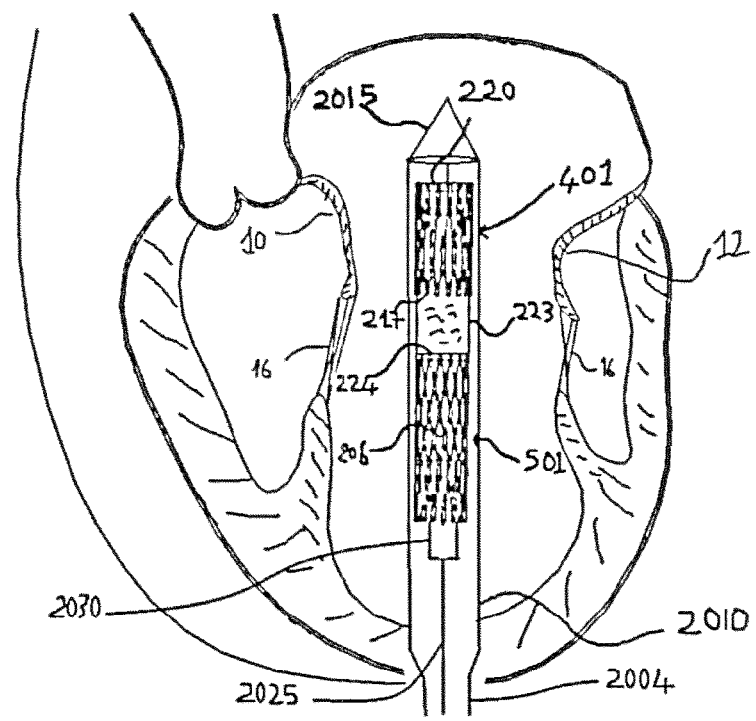
FIGS. 16A-16D illustrate how the device of FIG. 9 can be deployed at the mitral annulus of a patient's heart using a transapical delivery system.
Figure 16B:
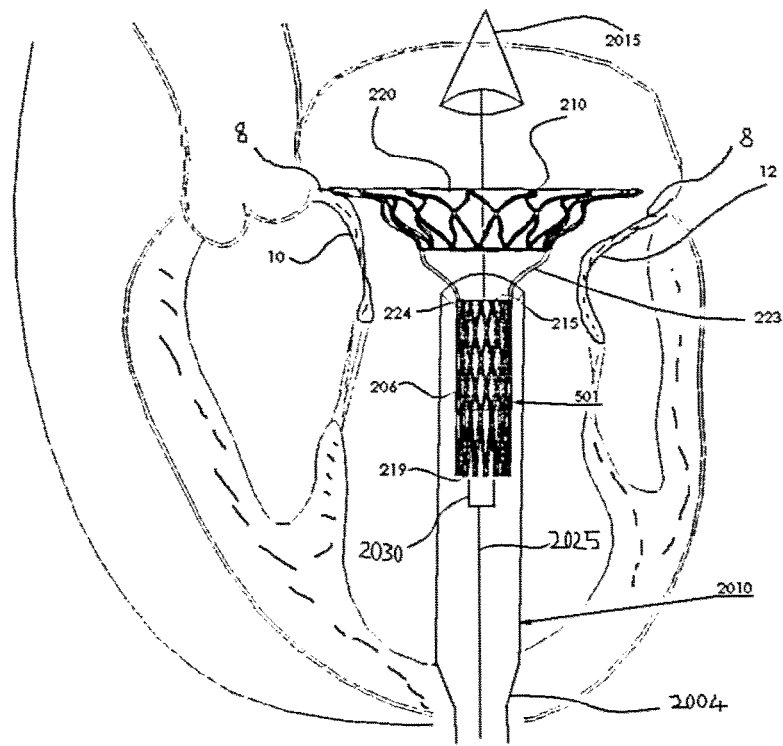
Figure 16C:
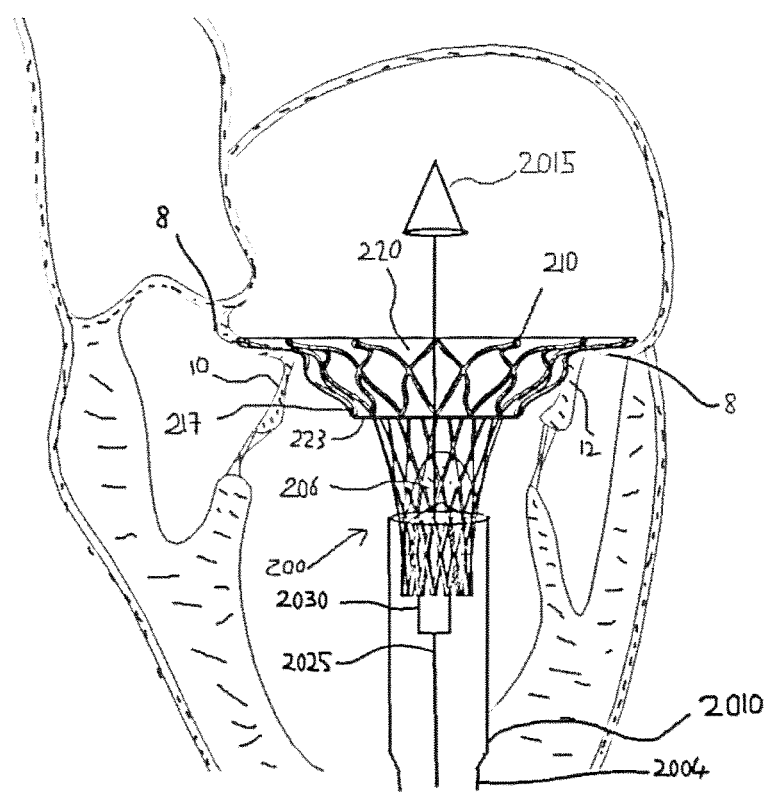
Figure 16D:
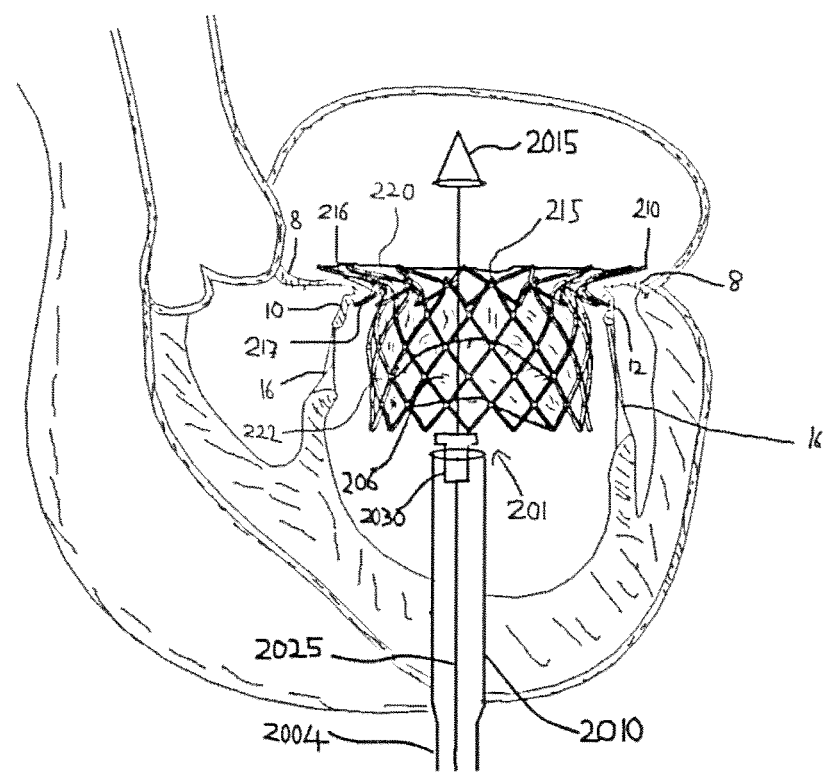

Referring now to FIG. 16A, the device 200 is shown in a collapsed configuration being delivered to the mitral annulus inside the capsule 2010. In FIG. 16B, the capsule 2010 is withdrawn (i.e., moved downwardly) with respect to the inner core 2025 to partially expose the device 200 so that the self-expanding wire frame will deploy the anchor piece 204 in the atrium, and at a location above the native annulus 8. In FIG. 16C, the capsule 2010 is shown as being further withdrawn to release the valve support piece 208. FIG. 16D shows the device 200 being fully deployed at the native annulus 8, and with the capsule 2010 and outer shaft 2015 being withdrawn with the rest of the delivery system.

Thus, when the device 200 is deployed, the native annulus 8 is captured or received in the space S2 between the tips 210 and 217 to create a "seal" to prevent leakage (blood flow back from the left ventricle to the left atrium) from the area surrounding the device 200. In addition, the tips 217 push aside the native anterior leaflet 10 and the native posterior leaflet 12 against the wall of the ventricle.

The devices 100 and 200 of the present invention provide a number of benefits. First, the manner in which the device 100 is anchored to the native annulus 8 allows the chordae to be free. Second, the devices 100 and 200 do not block blood flow to the aortic valve. Specifically, when the anchor piece 204 is first deployed at the native annulus, it functions as a secure anchor ring after the valve support piece 208 is inserted and moved up by at least 10 mm. As a result, it is possible to provide the cylindrical body 201 with a short length that minimizes blockage of blood flow. Third, the anchor piece 204 functions as an annulus ring to prevent rocking of the device 200 when the valves open and close, because the device 200 is provided in two separate pieces 204 and 208.

Even though the present invention has been described in connection with use as a mitral replacement valve, the devices 100 and 200 can also be used as an aortic or tricuspid valve. Specifically, when used as an aortic valve, the device 100 or 200 can be reversed by 180 degrees. The tricuspid location is the same as the mitral position, so the same principles described above would apply as well.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A heart valve assembly, comprising:
   an anchor section having an annular ring of cells that are configured to define an annular concave belt having a peripheral inflow end and a peripheral outflow end, with an anchor neck region defined between the inflow end and the outflow end;
   a valve support section having a generally cylindrical body with a concave neck area provided adjacent an outflow end, wherein the anchor section and the valve support section are provided in separate pieces and coupled together when the concave neck area of the cylindrical body is inserted through the anchor section and the outflow end of the valve support section is coupled to the outflow end of the anchor section, and wherein the anchor neck region of the anchor section and the concave neck area of the valve support section overlap each other when the anchor section is coupled with the valve support section, forming a neck section of the heart valve assembly; and
   a leaflet assembly having a plurality of leaflets that are stitched to the cylindrical body and which are positioned on an inflow side of the neck section.

2. The assembly of claim 1, wherein the valve support section has an inflow end that is configured with an annular zig-zag arrangement that defines peaks and valleys.

3. The assembly of claim 1, wherein the anchor neck region is configured as an annular U-shaped section.

4. The assembly of claim 3, wherein the concave neck area of the valve support section is seated inside the anchor neck region.

5. The assembly of claim 1, wherein the plurality of leaflets comprises three or four leaflets.

6. The assembly of claim 1, further including a plurality of skirts connected to the anchor section and the valve support section.

7. The assembly of claim 1, wherein the peripheral outflow end of the anchor section is configured with an annular zig-zag arrangement that defines peaks and valleys.

8. A heart valve assembly, comprising:
   an anchor section having an annular ring of cells that are configured to define an annular concave belt having a peripheral inflow end and a peripheral outflow end that comprises an arrangement of alternating tips and valleys that define inflection points, with an anchor neck region defined between the inflow end and the outflow end; and
   a valve support section having a generally cylindrical body with a concave neck area provided adjacent an outflow end, and outflow tips provided along the outflow end, wherein the anchor section and the valve support section are provided in separate pieces, and the concave neck area of the cylindrical body is inserted through the anchor section and the outflow tips are engaged with the inflection points at the outflow end of the anchor section to couple the valve support section to the anchor section, forming a neck section of the heart valve assembly; and
   a leaflet assembly having a plurality of leaflets that are stitched to the cylindrical body and which are positioned on an inflow side of the neck section.

9. The assembly of claim 8, wherein the valve support section has an inflow end that is configured with an annular zig-zag arrangement that defines peaks and valleys.

10. The assembly of claim 8, wherein the anchor neck region is configured as an annular U-shaped section.

11. The assembly of claim 10, wherein the concave neck area of the valve support section is seated inside the anchor neck region.

12. The assembly of claim 8, wherein the plurality of leaflets comprises three or four leaflets.

13. The assembly of claim 8, further including a plurality of skirts connected to the anchor section and the valve support section.

* * * * *